US012691076B2

(12) United States Patent
Nanovskaya et al.

(10) Patent No.: US 12,691,076 B2
(45) Date of Patent: Jul. 28, 2026

(54) METHODS AND COMPOSITIONS RELATED TO EXTRACELLULAR VESICLES

(71) Applicant: Board of Regents, the University of Texas System, Austin, TX (US)

(72) Inventors: Tatiana Nanovskaya, Galveston, TX (US); Erik Rytting, Galveston, TX (US); Mansi Shah, Galveston, TX (US); Svetlana Patrikeeva, Galveston, TX (US); Xiaoming Wang, Galveston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 17/355,290

(22) Filed: Jun. 23, 2021

(65) Prior Publication Data

US 2021/0393536 A1 Dec. 23, 2021

Related U.S. Application Data

(60) Provisional application No. 63/042,894, filed on Jun. 23, 2020.

(51) Int. Cl.
| *A61K 9/50* | (2006.01) |
| *A61K 35/50* | (2015.01) |
| *A61K 45/06* | (2006.01) |

(52) U.S. Cl.
CPC ............ *A61K 9/5068* (2013.01); *A61K 35/50* (2013.01); *A61K 45/06* (2013.01)

(58) Field of Classification Search
CPC ....... A61K 9/5068; A61K 35/50; A61K 45/06
See application file for complete search history.

(56) References Cited

FOREIGN PATENT DOCUMENTS

| WO | WO-2014193999 A2 * | 12/2014 | ........... C12N 15/111 |
| WO | WO-2018195338 A1 * | 10/2018 | ......... A61K 31/4418 |
| WO | WO-2019050998 A1 * | 3/2019 | ......... A61K 38/1808 |

OTHER PUBLICATIONS

Familari, M., et al., "Placenta-derived extracellular vesicles: their cargo and possible functions," Reproduction, Fertility, and Development 29(3): 433-447. doi: 10.1071/RD15143. (Year: 2017).*

Niu, Z., et al., PLoS One 12(10): e0186534 (2017). doi: 10.1371/journal.pone.0186534. (Year: 2017).*
Kim, M. S., et al., "Engineering macrophage-derived exosomes for targeted paclitaxel delivery to pulmonary metastases: in vitro and in vivo evaluations," Nanomedicine 14(1): 195-204. doi: 10.1016/j.nano.2017.09.011. Epub Oct. 2, 2017. (Year: 2017).*
Wang, J., et al., "Challenges in the development and establishment of exosome-based drug delivery systems," J Control Release 329: 894-906. doi: 10.1016/j.jconrel.2020.10.020. Epub Oct. 12, 2020. (Year: 2020).*
Kaur, G., and Verma, N., "Nature curing cancer - review on structural modification studies with natural active compounds having anti-tumor efficiency," Biotechnol Rep (Amst) 6:64-78. doi: 10.1016/j.btre.2015.01.005. (Year: 2015).*
Li, H., et al., "Amplification of anticancer efficacy by co-delivery of doxorubicin and lonidamine with extracellular vesicles," Drug Deliv 29(1):192-202. doi: 10.1080/10717544.2021.2023697. (Year: 2022).*
Auquière, M., et al., "Methods and Challenges in Purifying Drug-Loaded Extracellular Vesicles," J Extracell Vesicles 14(6):e70097. doi: 10.1002/jev2.70097. (Year: 2025).*
Lotvall et al., Journal of extracellular vesicles. 2014; 3:26913.
Nabers et al., Thorax. 1990; 45(5):416-418.
Tong et al., Reproduction (Cambridge, England). 2017; 153(6):835-845.
Kim et al., Nanomedicine : nanotechnology, biology, and medicine. 2016; 12(3):655-664.
Saari et al., Journal of controlled release. 2015; 220(Pt B):727-737.
Kalra et al., Proteomics. 2013; 13(22):3354-3364.
Wiklander et al., Journal of extracellular vesicles. 2015; 4:26316.
Johnsen et al., Biochimica et biophysica acta. 2014; 1846(1):75-87.
Mulcahy et al., Journal of extracellular vesicles. 2014; 3.
Agrawal et al., Nanomedicine: nanotechnology, biology, and medicine. 2017; 13(5):1627-36.
Yang et al., Pharmaceutical research. 2015; 32(6):2003-2014.
Smith et al., Nature. 1974; 252(5481):302-303.
Gupta et al., Placenta. 2005; 26(1):59-66.
Tannetta et al., PloS one. 2013; 8(2):e56754.
Southcombe et al., PloS one. 2011; 6(5):e20245.
Nanovskaya et al., The Journal of pharmacology and experimental therapeutics. 2002; 300(1):26-33.
Nanovskaya et al., American journal of obstetrics and gynecology. 2013; 209(4):373.
Hemauer et al., Biochemical pharmacology. 2009; 78(9):1272-1278.
Afrouzian et al., Biochemical pharmacology. 2018; 156:467-478.
Lapaire et al., Placenta. 2007; 28(1):1-5.

* cited by examiner

*Primary Examiner* — Tracy Vivlemore
*Assistant Examiner* — Eric J Rogers

(57) ABSTRACT

Certain embodiments are directed to methods and compositions related to delivery of therapeutic agents via syncytiotrophoblast-derived extracellular vesicles (EVs).

4 Claims, 5 Drawing Sheets

METHODS AND COMPOSITIONS RELATED TO EXTRACELLULAR VESICLES

PRIORITY PARAGRAPH

This Application claims priority to U.S. Provisional Patent Application Ser. No. 63/042,894 filed Jun. 23, 2020, which is incorporated herein by reference in its entirety.

STATEMENT REGARDING FEDERALLY FUNDED RESEARCH

None.

BACKGROUND

Lower respiratory tract infections (LRIs) and their complications are a substantial public health problem and a leading cause of illness and death in people of all ages. Previous estimates found that in 2013, LRIs caused more than 2.6 million deaths worldwide, making them the fifth leading cause of death overall and the leading infectious cause of death in children younger than 5 years. LRI is a term often used as a synonym for pneumonia but can also include bronchitis, bronchiolitis, and tuberculosis. Complications of LRIs may include pulmonary fibrosis.

Pneumonia is a leading cause of hospitalization and mortality in the United States, especially among elderly and immunosuppressed populations. Treatment of lung infections relies on rapid and accurate detection of the offending pathogen. The most common causes of typical bacterial infections of the lung are *S. pneumonia, S. aureus, H. influenza, Klebsiella*; atypical bacterial infections are *Mycoplasma, Chlamydophilia pneumonia, Chlamydia psittaci, Legionella*, and viral infections are influenza, para-influenza viruses, respiratory syncytial virus (RSV), adenovirus, coronaviruses (SARS-CoV, MERS-CoV, SARS-CoV-2), Cytomegalovirus (CMV), Herpes simplex virus, Varicella-zoster virus; and fungal infections are *Coccidiomycosis, Histoplasmosis, Blastomycosis, Cryptococcus*, and *Pneumocystis Jirovecii*.

Tuberculosis (TB) is an infectious disease caused by bacteria *Mycobacterium tuberculosis*. Despite the gains in tuberculosis control and the decline in both new cases and mortality, TB still accounts for a huge burden of morbidity and mortality worldwide. The bulk of the global burden of new infection and tuberculosis death is borne by developing countries, accounting for 60% of TB death in 2015. Tuberculosis remains a significant cause of both illness and death in developed countries, especially among individuals with a suppressed immune system. People with HIV are particularly vulnerable to death due to tuberculosis. Tuberculosis accounted for 35% of global mortality in individuals with HIV/AIDS in 2015.

Depending on the cause, antibiotics, antiviral, antifungal, and antimycobacterial drugs may be used treat LRIs. However, the systemic use of these medications may be associated with side effects of different severity. Thus, the development of vehicles for targeted delivery of antimicrobial, antiviral, antifungal, and antimycobacterial drugs to treat LRIs will decreased adverse effects associated with their systemic administration.

Lung cancer is the leading cause of cancer-related mortality in the United States.[4] Non-small cell lung cancer (NSCLC) accounts for >80% of all lung cancer cases and most patients with NSCLC are diagnosed with advanced cancer.[6] While surgical resection offers the best opportunity for long-term survival and cure in patients with resectable NSCLC, treatment options for patients with advanced unresectable disease include cytotoxic chemotherapy, molecularly targeted agents, and immunotherapy. Chemotherapy for non-small cell lung cancer often involves the administration of a cisplatin-based doublet or carboplatin plus paclitaxel. The side effects of systemic chemotherapy may have potential negative effects on quality of life both during and after treatment. While toxicities vary depending upon the therapeutic regimen used, chemotherapy-induced nausea and vomiting of variable severity may be seen with most chemotherapeutic regimens. Other effects include hematologic toxicity, including anemia and neutropenia with increased risks of infection. Nephrotoxicity and neurotoxicity are especially frequent with cisplatin.[7] Thus, the development of vehicles for targeted delivery of cytotoxic drugs to lung tumors with decreased adverse effects on other systems is of high importance.

There remains a need for additional vehicles and methods for efficient delivery of drugs to the lungs while minimizing adverse effects.

SUMMARY

A solution to the problems associated with delivery of drugs to the lungs is syncytiotrophoblast-derived extracellular vesicles (EVs) and their use as delivery vehicles. In certain aspects, syncytiotrophoblast-derived EVs can be used for distribution or administration of drugs to lung tissue. For example, in certain aspects, syncytiotrophoblast-derived EVs loaded with paclitaxel will increase delivery of the drug to the lung and can overcome multidrug drug resistance in cancer cells. Moreover, in addition to improved efficacy of the drug, the targeted delivery of paclitaxel can decrease off-target adverse effects associated with its administration.

The EV isolation methods described herein differ from the methods reported by Tong et al. in that villous tissue from term placenta is used rather than tissue from the first trimester, which results in differences in vesicle surface protein expression. Techniques have been developed for loading paclitaxel into nanovesicles enabling the incorporation of more paclitaxel (40% by mass) into the EVs than what has been previously reported in the literature.[8,20,21] The syncytiotrophoblast-derived EVs combines the advantages of lung distribution and overcoming P-glycoprotein-mediated drug resistance to increase the delivery of paclitaxel to lung cancer cells as compared to current therapeutic options.

One aspect of the current disclosure is the development of a biologically-inspired drug delivery system to target the lung, based on nano-sized extracellular vesicles (EVs) isolated from human placental syncytiotrophoblast. The anti-cancer agent paclitaxel, as an example, can be successfully loaded into these nanovesicles and achieve preferential distribution to the lung. Novel nanocarriers based on this strategy are expected to improve the treatment of various diseases of the lung, lower respiratory tract infections, and lung cancer. Due to the unique patterns of protein expression in two types of nanovesicle populations (DPPL-EVs and AVT-EVs, prepared from dual perfusion of placental lobule (DPPL), or agitation of villous tissue (AVT), respectively), differences may be observed in the distribution and therapeutic efficacy of drug-loaded EVs.

Certain embodiments are directed to methods to treat lung diseases based on administering syncytiotrophoblast-derived extracellular vesicles (EVs) comprising therapeutic agents efficacious against a disease of the lung to a subject in need thereof.

Certain embodiments are directed to methods of treating a disease of the lung and/or delivering a therapeutic agent to the lung comprising administering syncytiotrophoblast-derived extracellular vesicles (EVs) derived from full term placenta comprising therapeutic agents to the lung to a subject in need thereof. At term placenta is discoid in shape with a diameter of 15-25 cm, approximately 3 cm thick and weighs about 500-600 g. At birth, it is torn from the uterine wall and around 30 minutes after the birth of the child it is expelled from the uterine cavity. A full-term placenta is one that is acquired after a vaginal or caesarian birth of a child at ≥37 weeks gestation or longer. The therapeutic agent can be alemtuzumab, altretamine, aminoglutethimide, amsacrine, anastrozole, azacitidine, bleomycin, bicalutamide, busulfan, capecitabine, carboplatin, carmustine, celecoxib, chlorambucil, 2-chlorodeoxyadenosine, cisplatin, colchicine, cyclophosphamide, cytarabine, cytoxan, dacarbazine, dactinomycin, daunorubicin, docetaxel, doxorubicin, epirubicin, estramustine phosphate, etodolac, etoposide, exemestane, floxuridine, fludarabine, 5-fluorouracil, flutamide, formestane, gemcitabine, gentuzumab, goserelin, hexamethylmelamine, hydroxyurea, hypericin, ifosfamide, imatinib, interferon, irinotecan, letrozole, leuporelin, lomustine, mechlorethamine, melphalen, mercaptopurine, 6-mercaptopurine, methotrexate, mitomycin, mitotane, mitoxantrone, nilutamide, nocodazole, paclitaxel, pentostatin, procarbazine, raltitrexed, rituximab, rofecoxib, streptozocin, tamoxifen, temozolomide, teniposide, 6-thioguanine, topotecan, toremofine, trastuzumab, vinblastine, vincristine, vindesine, vinorelbine, or a combination thereof. In other aspects, the therapeutic agent can be levofloxacin, clarithromycin, levaquin, ceftriaxone, azithromycin, doxycycline, amoxicillin, amoxicillin/clavulanate, ciprofloxacin, clindamycin, cefdinir, sulfamethoxazole/trimethoprim, cefotaxime, metronidazole, cefuroxime, moxifloxacin, ceftin, vancomycin, ceftazidime, amikacin, cefepime, cefpodoxime, cilastatin/imipenem, erythromycin, linezolid, cefazolin, piperacillin/tazobactam, cefixime, dicloxacillin, tetracycline, tobramycin, ampicillin, bacitracin, cefaclor, cefprozil, ertapenem, gentamicin, ofloxacin, tigecycline, ampicillin/sulbactam, avibactam/ceftazidime, aztreonam, cefditoren, cefotetan, cefoxitin, ceftaroline, ceftolozane/tazobactam, delafloxacin, gemifloxacin, lefamulin, nafcillin, omadacycline, oxacillin, penicillin G potassium, penicillin G sodium, piperacillin, telavancin, oseltamivir, zanamivir, peramivir, ribavirin, amantadine/rimantadine, interferon alpha, acyclovir, ganciclovir, cidofovir, chloroquine, hydroxychloroquine, lopinavir/ritonavir, favipiravir, remdesivir, efavirenz, atazanavir, baricitinib, tocilizumab, acalabrutinib, saquinavir, lamivudine, dolutegravir, asunaprevir, simeprevir, grazoprevir, daclatasvir, etravirine, entecavir, abacavir, penciclovir, trifluridine, danoprevir, telaprevir, darunavir, nelfinavir, indinavir, boceprevir, lomibuvir, raltegravir, amphotericin B, intraconazole, flucytosine, fluconazolem rifampin, rifabutin, isoniazid, prrazinamide, ethambutol, pirfenidone, nintedanib, streptomycin, or a combination thereof. The EVs can have an average diameter of 50 to 800 nm. In certain aspects, the EVs comprise placental alkaline phosphatase (PLAP). In a further aspect, the EVs further comprise one or more proteins selected from or all or a combination of CD81, CD9, CD63, tumor susceptibility gene (TSG) 101, programmed cell death 6-interacting protein (PDCD/ALIX), efflux transporter P-gp, and/or efflux transporter BCRP. The EVs can further comprise a cellular or biological targeting agent. In certain aspects, the targeting agent is covalently coupled to the EV. In a further aspect, the targeting agent is couple to the EV via a linker. The EVs can be administered by inhalation, parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration.

Certain embodiments are directed to Syncytiotrophoblast-derived extracellular vesicles (EVs) comprising placental alkaline phosphatase; exosomal markers CD81, CD9, CD63, tumor susceptibility gene 101, and programmed cell death 6-interacting protein (ALIX); and efflux transporters P-gp and BCRP. In certain aspects, the EVs can have an average diameter of 50, 100, 150, 200, 250, 300, 350, 400, 450, 500, 550, 600, 650, 700, 750, to 800 nm, +/−10% including all values and ranges there between.

Other embodiments are directed to methods for producing syncytiotrophoblast-derived extracellular vesicles (EVs) comprising: (a) obtaining and perfusing a full term placenta; (b) collecting a maternal perfusate; and (c) isolating extracellular vesicles from the maternal perfusate. The methods can further comprise loading the isolated extracellular vesicles with a therapeutic agent. The EVs can be prepared by dual-perfusion of placental lobule (DPPL) or agitation of villous tissue (AVT).

As used herein, the term "extracellular vesicles", "extracellular-vesicles" or "EVs" refers to extracellular vesicles that are membrane surrounded structures based on membranes or fragments originating from syncytiotrophoblast cells.

As used herein, the term "syncytiotrophoblast-derived extracellular-vesicles" refers to extracellular vesicles that are created using membranes or membrane fragments obtained from the syncytiotrophoblasts or that are released or secreted by the syncytiotrophoblasts.

As used herein, the term "dose" or "unit dose" means the amount of a medication that is administered or is to be administered to a subject, e.g., a human, in a single dose.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value (+/−5%).

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a chemical composition and/or method that "comprises" a list of elements (e.g., components or features or steps) is not necessarily limited to only those elements (or components or features or steps), but may include other elements (or components or features or steps) not expressly listed or inherent to the chemical composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a chemical composition and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
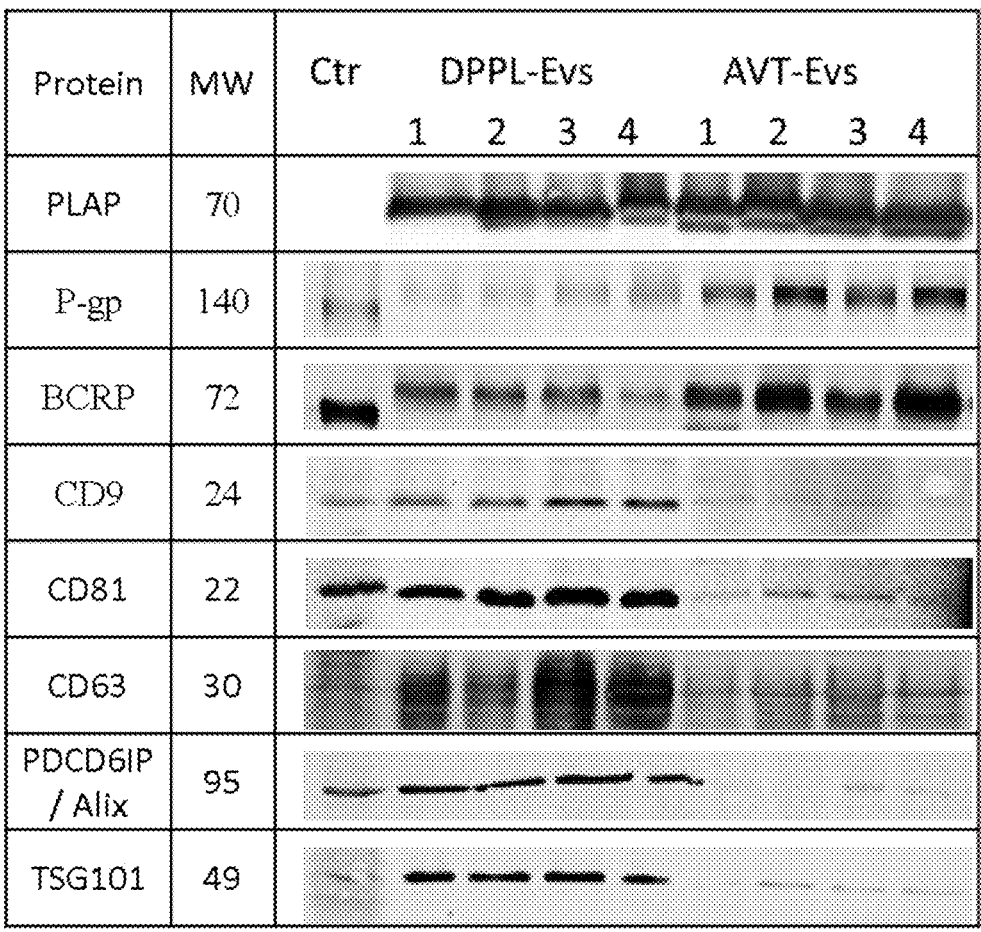
FIG. 1. Comparative expression of syncytiotrophoblast marker (PLAP), exosomal markers (CD81, CD9, CD63, TSG101, and ALIX), and efflux transporters (P-gp and BCRP) in isolated DPPL-EVs and apical AVT-EVs. The well labels (1, 2, 3, 4) correspond to matched individual placentas, i.e., the DPPL-EVs in lane 1 and the apical AVT-EVs in lane 1 were prepared from the same placenta.

The following discussion is directed to various embodiments of the invention. The term "invention" is not intended to refer to any particular embodiment or otherwise limit the scope of the disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

I. EXTRACELLULAR VESICLE (EV) DELIVERY VEHICLES

Extracellular vesicles—including exosomes—have been explored as alternative drug delivery vehicles.[8,9] Advantages of an exosome-based drug delivery system over existing synthetic systems include their innate biocompatibility,[10] increased stability in the blood circulation compared to other nanoformulations,[11] and potential for targeted drug delivery.[8,9,12]

While exosomes could be released by many cells, the choice of donor cell type is one of the main considerations in the development of an exosome-based drug delivery system.[13] The isolated exosomes should be tissue-specific, non-immunogenic, non-inflammatory, non-toxic, stable in the blood circulation, capable of delivering their cargo through normal administration routes, and capable of carrying a sufficient amount of therapeutic drug.[13]

Certain embodiments described herein are directed to a biologically-inspired drug delivery system to target the lung, based on nano-sized extracellular vesicles (EVs) derived from human placental syncytiotrophoblast.

The human placenta is an organ of fetal origin that develops and functions in direct contact with the maternal bloodstream. Being in direct contact with maternal blood, placental EVs can travel long distances within the body. The localization of placentally derived cells in maternal lungs was first described in 1893 by Dr. Schmorl, who performed autopsies of 17 bodies of deceased pregnant women affected with eclampsia.[1] The lung is also the primary site for metastases of the placental trophoblastic cancer choriocarcinoma. The metastases were found more frequently in the lungs (80% of reviewed cases), while the metastases occurred less frequently in the vagina (30%), pelvis (20%), and brain (10%).[2]

In a recent study, the distribution of macro-EVs (average size $72\pm21$ μm) and micro-EVs ($290\pm72$ nm) isolated from cultured human first trimester placental explants was studied following their intravenous injection to non-pregnant and pregnant mice.[3] The authors found that while macro-EVs were localized to the lungs in both groups of studied animals, the distribution of micro-EVs was time dependent and differed between non-pregnant and pregnant animals. In non-pregnant animals, micro-EVs were localized primarily in the lungs after 2 minutes of exposure; in the lungs, liver, and kidneys after 30 minutes of exposure; and in the liver and kidneys after 24 hours. In pregnant animals, micro-EVs were localized primarily in the lungs after 30 min of exposure, and predominantly in the lungs and the liver after 24 hours of exposure.[3] Furthermore, these authors did not find placental EVs in the spleen, which was the primary organ for distribution of similarly sized synthetic beads used as control, suggesting that localization of placental EVs in the lungs is most likely associated with particular properties of the vesicles. The migration of syncytiotrophoblast-derived EVs to the lungs make them a promising biologically-inspired vehicle for chemotherapeutic drugs to target lung cancer.

In order to demonstrate the targeted distribution of placentally derived EVs in lung tissue as well as the efficacy of these vehicles to deliver therapeutic drugs to treat lung diseases, paclitaxel is used as a model drug. Paclitaxel was chosen for two reasons: (1) This allows for the comparison of our paclitaxel-loaded EVs to Abraxane®, an albumin-bound nanoformulation of paclitaxel which has been approved by the FDA for the treatment of NSCLC in combination with carboplatin. (2) Paclitaxel is a substrate of P-glycoprotein (P-gp). This allows for the potential of nanovesicle formulations to overcome P-gp-mediated drug resistance in lung cancer cells.

Using resistant MDR cells expressing P-gp (MDCK-MDR1), it has been shown that paclitaxel loaded into macrophage-derived exosomes significantly increased drug cytotoxicity as compared to free paclitaxel.[8] Furthermore, when the authors expressed the cytotoxicity of the drug in the form of a resistance reversion index (RRI, the ratio of the IC50 of free paclitaxel/the IC50 of paclitaxel in the nano-formulations), they found that the cytotoxicity of the exosomal formulation of paclitaxel was considerably greater in resistant cells (RRI>53.33) than in sensitive cells (RRI=18.35).[8] On the other hand, for the commercially available formulation Taxol®, the RRI in both resistant (RRI>5.85) and sensitive cancer cells (RRI=6.17) did not differ significantly. These data suggest an advantage of exosome-like drug delivery systems over a traditional surfactant-based formulation of paclitaxel in cells overexpressing P-gp. Previously, it was suggested that due to the presence of adhesion proteins, tetraspanins, integrins, immunoglobulins, proteoglycans, and lectins, exosomes may have advantages over other nanoformulations in treating tumors.[19] Moreover, because exosomes consist of cellular membranes, they also have an ability to fuse with the plasma membranes, thus bypassing P-gp mediated efflux.[8] Importantly, the exosomes themselves did not inhibit P-gp, which potentially could decrease drug toxicity associated with non-specific inhibition of P-gp in other organs.

One of the major impediments to successful drug therapy—for example, the use of paclitaxel for treating lung cancer—is P-glycoprotein-mediated drug resistance. However, based on the recently published study by Kim et al,[8] it appears that the use of exosome-like drug delivery systems will provide a new opportunity to overcome P-gp-mediated drug resistance.

Certain embodiments of the current invention relate to extracellular vesicles derived from syncytiotrophoblast, wherein the extracellular vesicles are essentially free of vesicles not derived from the syncytiotrophoblast. Furthermore, aspects of the present invention relate to a pharmaceutical composition for use in the treatment of lung diseases, e.g., lung cancer, lower respiratory tract infections, including pneumonia, bronchitis, bronchiolitis and tuberculosis, wherein the pharmaceutical composition comprises extracellular vesicles derived from syncytiotrophoblast (syncytiotrophoblast-derived EVs).

The present invention also relates to a method of treating lung diseases, e.g., lung cancer, lower respiratory tract infections, including pneumonia, bronchitis, bronchiolitis and tuberculosis, the method including the administration of a pharmaceutical composition comprising extracellular vesicles derived from syncytiotrophoblast. In certain aspects, the extracellular vesicles are essentially free of vesicles not derived from syncytiotrophoblast.

Furthermore, the syncytiotrophoblast-derived extracellular-vesicles of the invention are positive for exosome-enriched markers CD9, CD81, CD63, PDCD6IP/ALIX, and TSG101 and optionally wherein the syncytiotrophoblast-derived EVs are negative for CD41, CD235a/b, or CD45.

The protein content of the extracellular vesicles can be determined by various techniques, which are suitable to determine the protein content, e.g., Western Blot, or mass spectrometer based techniques. For such an analysis, the extracellular vesicles are collected and are lysed. A respective amount of the protein lysate is analyzed by SDS-PAGE. After blotting, the membrane is incubated with the respective antibodies and the level of the binding is determined. The antibodies can be diluted in buffer containing non-fat dry milk, and can be incubated, e.g., at room temperature for 4 hours. After washing with an appropriate buffer, a secondary antibody can be diluted in an appropriate buffer. Proteins can be detected using an appropriate detection agent(s), e.g., ECL Prime Western Blotting Detection Reagent (RPN2232, GE Healthcare) and ChemiDoc MP System (Bio-Rad).

Accordingly, the cell surface markers may be used to characterize the extracellular vesicles. Surface marker expression can be analyzed by various techniques, which are suitable to determined surface markers. For example, fluorescence activated cell sorting (FACS) can be used to assess surface markers.

Further, the extracellular vesicles of the invention have a particular size. The extracellular vesicles of the invention may have a diameter in range from about 50, 60, 70, 80, 90. 100. 150, 200, 250, 300, 350, 400, 450, 500, 550, 600, 650, 700, 750 nm up to about 800 nm, including all values and ranges there between.

In order to determine the size of the extracellular-vesicles of the invention, various techniques can be employed that are suitable to determine the average size of membrane vesicles. For example, nanoparticle tracking analysis (NTA) can be performed.

The invention also relates to the pharmaceutical composition, the extracellular vesicles, and/or the extracellular vesicles obtained by the methods for use as a medicament. In particular, the invention relates to the pharmaceutical composition, the extracellular vesicles, or the medium comprising the extracellular vesicles for use in the treatment of one or more of the diseases and/or disorders including diseases of the lung.

The dose of the extracellular vesicles or the extracellular vesicles comprised in the pharmaceutical composition may range from about $1 \times 10^6$, $1 \times 10^7$, $1 \times 10^8$, $1 \times 10^9$, $1 \times 1^{10}$, $1 \times 10^{11}$, $1 \times 10^{12}$, $1 \times 10^{13}$, $1 \times 10^{14}$, $1 \times 10^{15}$, $1 \times 10^{16}$, $1 \times 10^{17}$, $1 \times 10^{18}$, to $2 \times 10^{19}$ particles, including all values and ranges there between. The particle number or dose of the extracellular vesicles may be determined by NTA. The dose of the extracellular vesicles may also be higher or lower than indicated above as long as the dose treats a disease of the lung.

The pharmaceutical compositions provided herein can be administered to the subject at a suitable dose. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently.

The administration of the herein provided compositions may, inter alia, comprise an administration twice daily, every day, every other day, every third day, every fourth day, every fifth day, once a week, once every second week, once every third week, once every month, etc.

EVs can be used to deliver therapeutic or imaging agents. In one embodiment, the invention provides an EV comprising, for example, paclitaxel. In other embodiments, an EV described herein comprises a conventional chemotherapeutic agent including, but not limited to, alemtuzumab, altretamine, aminoglutethimide, amsacrine, anastrozole, azacitidine, bleomycin, bicalutamide, busulfan, capecitabine, carboplatin, carmustine, celecoxib, chlorambucil, 2-chlorodeoxyadenosine, cisplatin, colchicine, cyclophosphamide, cytarabine, cytoxan, dacarbazine, dactinomycin, daunorubicin, docetaxel, doxorubicin, epirubicin, estramustine phosphate, etodolac, etoposide, exemestane, floxuridine, fludarabine, 5-fluorouracil, flutamide, formestane, gemcitabine, gentuzumab, goserelin, hexamethylmelamine, hydroxyurea, hypericin, ifosfamide, imatinib, interferons, irinotecan, letrozole, leuporelin, lomustine, mechlorethamine, melphalen, mercaptopurine, 6-mercaptopurine, methotrexate, mitomycin, mitotane, mitoxantrone, nilutamide, nocodazole, paclitaxel, pentostatin, procarbazine, raltitrexed, rituximab, rofecoxib, streptozocin, tamoxifen, temozolomide, teniposide, 6-thioguanine, topotecan, toremofine, trastuzumab, vinblastine, vincristine, vindesine, and vinorelbine. In other embodiments, an EV described herein comprises a conventional therapeutic agent or combination of agents used in the treatment of lower respiratory tract infections or their complications, including, but not limited to, levofloxacin, clarithromycin, levaquin, ceftriaxone, azithromycin, doxycycline, amoxicillin, amoxicillin/clavulanate, ciprofloxacin, clindamycin, cefdinir, sulfamethoxazole/trimethoprim, cefotaxime, metronidazole, cefuroxime, moxifloxacin, ceftin, vancomycin, ceftazidime, amikacin, cefepime, cefpodoxime, cilastatin/imipenem, erythromycin, linezolid, cefazolin, piperacillin/tazobactam, cefixime, dicloxacillin, tetracycline, tobramycin, ampicillin, bacitracin, cefaclor, cefprozil, ertapenem, gentamicin, ofloxacin, tigecycline, ampicillin/sulbactam, avibactam/ceftazidime, aztreonam, cefditoren, cefotetan, cefoxitin, ceftaroline, ceftolozane/tazobactam, delafloxacin, gemifloxacin, lefamulin, nafcillin, omadacycline, oxacillin, penicillin G potassium, penicillin G sodium, piperacillin, telavancin, oseltamivir, zanamivir, peramivir, ribavirin, amantadine/rimantadine, interferon alpha, acyclovir, ganciclovir, cidofovir, chloroquine, hydroxychloroquine, lopinavir/ritonavir, favipiravir, remdesivir, efavirenz, atazanavir, baricitinib, tocilizumab, acalabrutinib, saquinavir, lamivudine, dolutegravir, asunaprevir, simeprevir, grazoprevir, daclatasvir, etravirine, entecavir, abacavir, penciclovir, trifluridine, danoprevir, telaprevir, darunavir, nelfinavir, indinavir, boceprevir, lomibuvir, raltegravir, amphotericin B, intraconazole, flucytosine, fluconazolem rifampin, rifabutin, isoniazid, prrazinamide, ethambutol, pirfenidone, nintedanib, and streptomycin.

Extracellular Vesicle Isolation, Loading, and Targeting: Syncytial EVs can be prepared using methods of dual-perfusion of placental lobule (DPPL) and agitation of villous tissue (AVT).

Dual-perfusion of placental lobule (DPPL). Normal term placentas can be obtained. Each placenta is immediately perfused via an umbilical artery and direct injection of the intervillous space with heparinized buffer or cell culture medium at pH 7.4 to preserve placental function and prevent clotting. A fetal artery and vein supplying a single cotyledon can be cannulated and perfused with buffer or cell culture medium. The intervillous space of the placenta is perfused by blunt tip needles. Maternal and fetal circulatory temperature and pH are maintained near 37° C. (±2° C.) and pH 7.4 (±0.2). The maternal flow rate was maintained at 12 to 15 ml/min and the fetal flow rate was in the range of 1.5-3.0 ml/min. Viability of the placenta can be monitored by glucose consumption and lactate production. After 3 hours of perfusion,[26,27] medium from maternal outflow was pelleted at 150,000×g.

Agitation of villous tissue (AVT). Placental EVs from brush border membranes were prepared according to an established protocol with a slight modification.[28,29] Placental tissue was gently dissected from the maternal side and washed three to four times in ice-cold saline (0.9% NaCl).

The tissue was transferred to Sucrose-HEPES-Tris (SHT) Buffer (250 mM sucrose, 10 mM HEPES-Tris, pH 7.4) containing 1 mM EDTA and stirred for 1 h to disrupt brush border membranes. The tissue suspension was filtered through mesh strainer with pore size of 250 µm. Suspension filtrate was used to prepare apical (brush border) membrane vesicles, and tissue residue was used to prepare basal membrane vesicles. Following agitation of villous tissue, the suspension filtrate was subjected to differential centrifugation steps (1,000×g for 10 minutes followed by 10,000×g for 15 minutes, followed by 46,000×g for 60 min) to isolate apical membranes.[28,29] The pellet was resuspended in SHT buffer using Wheaton 358044 15 ml Potter-Elvehjem Tissue homogenizer, and incubated on ice in SHT buffer containing 10 mM $MgCl_2$ for 20 minutes under continuous stirring followed by centrifugation at 3,000×g for 10 min at 4° C. Supernatant was then centrifuged at at 46,000×g for 60 min at 4° C., and the pellet containing apical AVT-EVs was resuspended in PBS Buffer using a 26-guage needle, aliquoted and stored at −80° C.[29]

Tissue residue in 50 mM Tris-HCl containing basal membranes was portioned and sonicated using a ¾ inch high-gain probe for 10 sec at 240 W (Vibra-cell, Sonics) on ice. Sonicated tissue was collected on a 250 µm mesh strainer, and stirred gently in 5 mM Tris-HCl, (pH 7.4) on ice for 1 hour. Tissue was collected again using the 250 µm mesh strainer, and gently stirred in SHT Buffer containing 1 mM EDTA on ice for 30 min. Portions were then sonicated twice at 240 W for 20 sec each, and centrifuged at 3000×g for 10 min at 4° C., followed by 10,000×g for 10 min at 4° C., followed by supernatant centrifugation at 46,000×g for 60 min at 4° C. Pellet containing basal membranes was resuspended in SHT Buffer, aliquoted and stored at −80° C.[29].

Basal AVT-EVs were further purified before use by discontinuous sucrose gradient of 35% sucrose (w/w) overlaid with 25% sucrose (w/w), modified from Afrouzian et al, 2018[29]. Crude vesicles were layered over sucrose solutions, and the sucrose gradient tubes were centrifuged at 141,000×g for 4 hours at 4° C. using a swinging bucket rotor (SW Ti40), followed by centrifugation of the interface between the 25/35% sucrose layers at 46,000×g for 60 min at 4° C. Pellet containing basal AVT-EVs was resuspended in SHT Buffer using a 26-guage needle, aliquoted and stored at −80° C.[29].

Methods for loading EVs with agent (polynucleotide or polypeptide or small molecule) can include sonication, lipofection, electroporation, covalent or non-covalent coupling to the EV surface, simple co-incubation as well as any standard transfection method. In particular embodiments, it may be useful to derivatize the EV with an antibody or other targeting moiety such as a polynucleotide or peptide or small molecule that selectively binds to a cellular or biological target of interest. Derivitization includes the covalent or non-covalent association of moiety to the EVs that is directly coupled or indirectly coupled via a linker to the EVs. Targeted EVs may be loaded with an agent intended to treat the disease of interest.

II. PHARMACEUTICAL COMPOSITIONS

The invention provides EVs for the delivery of therapeutic compositions that specifically deliver an agent. In one embodiment, the present invention provides a pharmaceutical composition comprising an EV derived from a syncytiotrophoblast cell. EVs of the invention may be administered as part of a pharmaceutical composition. In general, EVs are provided in a physiologically balanced saline solution. The solution comprising the EVs is stored at room temperature for up to about 24 hours, for longer than twenty four hours such solutions can be stored at about four degrees Celsius for days, weeks, or months. EVs are frozen for long term storage up to 10 years. The compositions should be sterile and contain a therapeutically effective amount of the EV in a unit of weight or volume suitable for administration to a subject.

EVs of the invention may be administered within a pharmaceutically-acceptable diluent, carrier, or excipient, in unit dosage form. Conventional pharmaceutical practice may be employed to provide suitable formulations or compositions to administer the compounds to patients suffering from a disease. Administration may begin before the patient is symptomatic. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" Ed. A. R. Gennaro, Lippincourt Williams & Wilkins, Philadelphia, Pa., 2000. The formulations can be administered to human patients in therapeutically effective amounts (e.g., amounts which prevent, eliminate, or reduce a pathological condition) to provide therapy for a disease or condition. The preferred dosage of an EV of the invention is likely to depend on such variables as the type and extent of the disorder, the overall health status of the particular patient, the formulation of the compound excipients, and its route of administration.

With respect to a subject having a neoplastic disease or disorder, an effective amount is sufficient to stabilize, slow, or reduce the proliferation of the neoplasm.

A variety of administration routes are available. The methods of the invention, generally speaking, may be practiced using any mode of administration that is medically acceptable, meaning any mode that produces effective levels of the active compounds without causing clinically unacceptable adverse effects. Other modes of administration include oral, rectal, topical, intraocular, buccal, intravaginal, intracisternal, intracerebroventricular, intratracheal, nasal, transdermal, within/on implants, e.g., fibers such as collagen, osmotic pumps, or grafts comprising appropriately transformed cells, etc., or parenteral routes.

III. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Characterization of the Placentally Derived Extracellular Vesicles (EVS)

Placentally derived extracellular vesicles (EVs) are characterized, including the in vitro stability and biocompatibility of blank EVs (unloaded, without drug) in both epithelial and endothelial lung cells. Successful drug loading of the EVs with paclitaxel by the sonication method is demonstrated, followed by the in vitro demonstration of the pharmacological effect of paclitaxel in reducing the cell viability of NCI-H441 lung cancer cells. Finally, pharmacokinetic tissue distribution studies were performed following tail-vein injection of 5 mg/kg of either paclitaxel-loaded apical AVT-EVs or Abraxane in CD-1 mice. Formulation of paclitaxel in the apical AVT-EVs resulted in 85-fold higher levels of the drug in lung tissue ($AUC_{0-8h}$) when compared to Abraxane.

TABLE 1

Physical characteristics of isolated EV populations.

| Population of EVs | Size (nm) | Polydispersity index (PDI) | ζ-potential (mV) |
|---|---|---|---|
| DPPL-EVs in PBS (pH 7.4) | 185 ± 3.5 | 0.25 ± 0.01 | −20.6 ± 1 |
| Apical AVT-EVs in PBS (pH 7.4) | 225 ± 1.5 | 0.23 ± 0.01 | −22.4 ± 0.6 |

Characterization of placentally derived extracellular vesicles. Currently there are three main methods for obtaining/isolating syncytial EVs: (1) agitation of villous tissue[22]; (2) Cultured primary trophoblast cells or placental explants[23]; and (3) Dual perfusion of placental lobule.[24,25] Data presented herein were obtained by preparing syncytial EVs using methods of dual-perfusion of placental lobule (DPPL) and agitation of villous tissue (AVT). Briefly, after 3 hours of perfusion,[26,27] medium from maternal outflow was pelleted at 150,000×g. Following agitation of villous tissue, the tissue suspension was subjected to differential centrifugation steps (1,000×g for 10 minutes followed by 10,000×g for 15 minutes, followed by 46,000×g for 60 min).[28,29] Apical AVT-EVs were pelleted after centrifugation at 46,000×g.[29] Following isolation, EVs were characterized by size and charge (Table 1). The EVs were also validated according to the requirements of the International Society for Extracellular Vesicles[30] (FIG. 1, Table 2).

The data in Table 1 show that isolated DPPL-EVs and apical AVT-EVs have similar physical properties. However, the ratio of protein to total mass in the DPPL-EVs was higher than in the apical AVT-EVs (34% vs 19%).

The data in FIG. 1 show a strong signal of PLAP determined by WB analysis in both populations of EVs, indicating that the isolated DPPL-EV and apical AVT-EVs originated from syncytiotrophoblast cells. Furthermore, the expression of the so-called exosome-enriched markers CD9, CD81, CD63, ALIX, and TSG101 is much stronger in DPPL-EVs than in apical AVT-EVs, while the expression of major efflux transporters P-gp and BCRP is stronger in apical AVT-EVs than in DPPL-EVs.

The data in Table 2 show that irrespective of the methods used to release placental EVs either by agitation of villous tissue or by dual placental perfusion, the purity of the preparations is very high, as contamination by intracellular membranes of mitochondria and endoplasmic reticulum is minimal.

TABLE 2

Purity of DPPL-EVs and apical AVT-EVs by assessment of the activity of intracellular membranes of mitochondria and endoplasmic reticulum.

| | Cytochrome C Oxidase activity (Units/mL) | Cytochrome C Reductase activity (mUnits/mL) |
|---|---|---|
| Placental fractions[†] | 0.145 ± 0.014[1] (100%) | 88.4 ± 16.2[2] (100%) |
| DPPL-EVs | 0.001 ± 0.001 (0.7 ± 0.1%) | 2.5 ± 1.1 (3 ± 1%) |
| Apical AVT-EVs | 0.004 ± 0.004 (2.5 ± 2.7%) | 3.6 ± 0.8 (4.0 ± 1%) |

Data are expressed as mean ± s.d.
[†]Placental fractions: crude mitochondrial[1]; crude microsomal[2]
[1]Percent contamination of DPPL-EVs and AVT-EVs by mitochondrial membranes was calculated relative to cytochrome C oxidase activity determined in crude mitochondrial preparations from human placentas.
[2]Percent contamination of DPPL-EVs and AVT-EVs by membranes of endoplasmic reticulum was calculated relative to cytochrome C reductase activity determined in crude microsomal preparations from human placentas.

Stability of the EVs. The stability of the EVs in PBS (pH 7.4) was investigated by evaluating the effect of storage temperatures 4° C. and 22° C. up to 28 days and up to 24 hours of incubation at 37° C. on placental EV size (FIG. 2) and surface charge (data not shown). For comparison to a relevant nano-sized drug carrier control, the same studies were also carried out using commercially prepared PEGylated liposomes.

Figure 2:
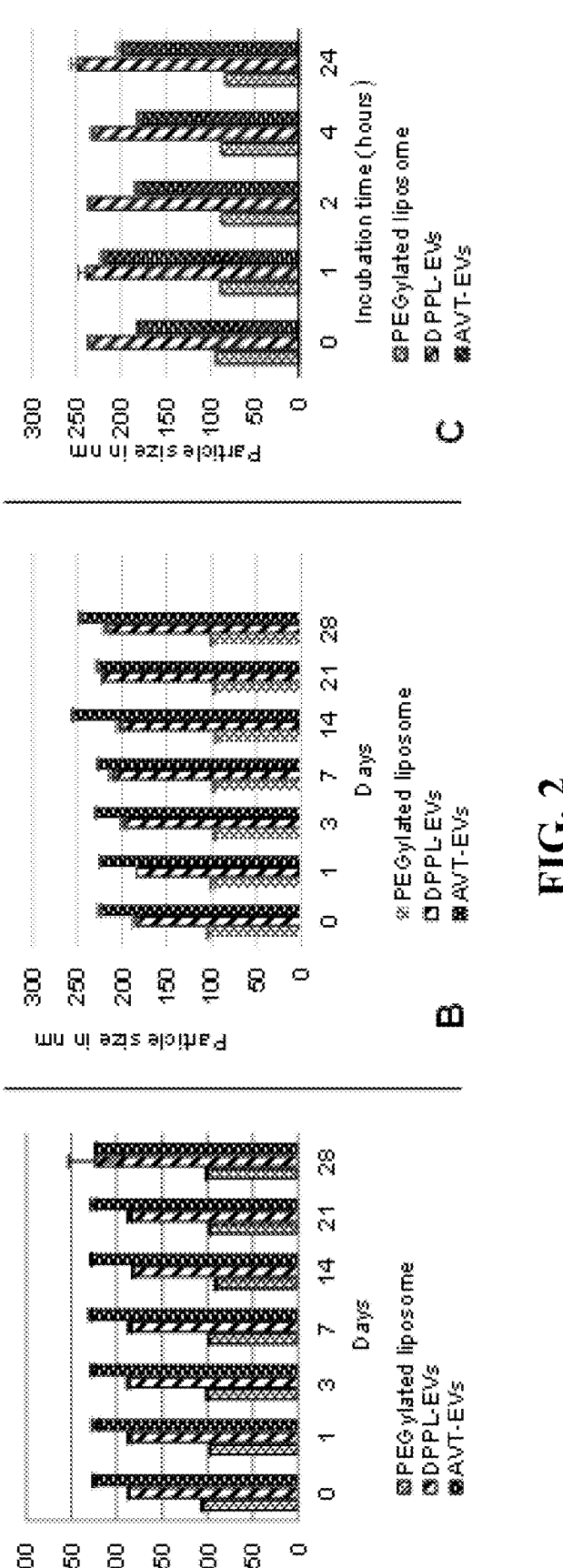
FIG. 2. Stability of DPPL-EVs and apical AVT EVs. Z-average particle size of isolated EVs following storage at 4° C. (A) and 22° C. (B) up to 28 days and after 1, 2, 4, and 24 hours of incubation at 37° C. (C) in PBS at pH 7.4.

The data in FIG. 2 show that neither storage at 4° C. and 22° C. up to 28 days nor 24 hours of incubation at 37° C. affected the size of DPPL-EVs and apical AVT-EVs, suggesting their stability at these conditions. Likewise, surface charge (zeta potential) was not significantly changed at these temperatures.

Figure 3:
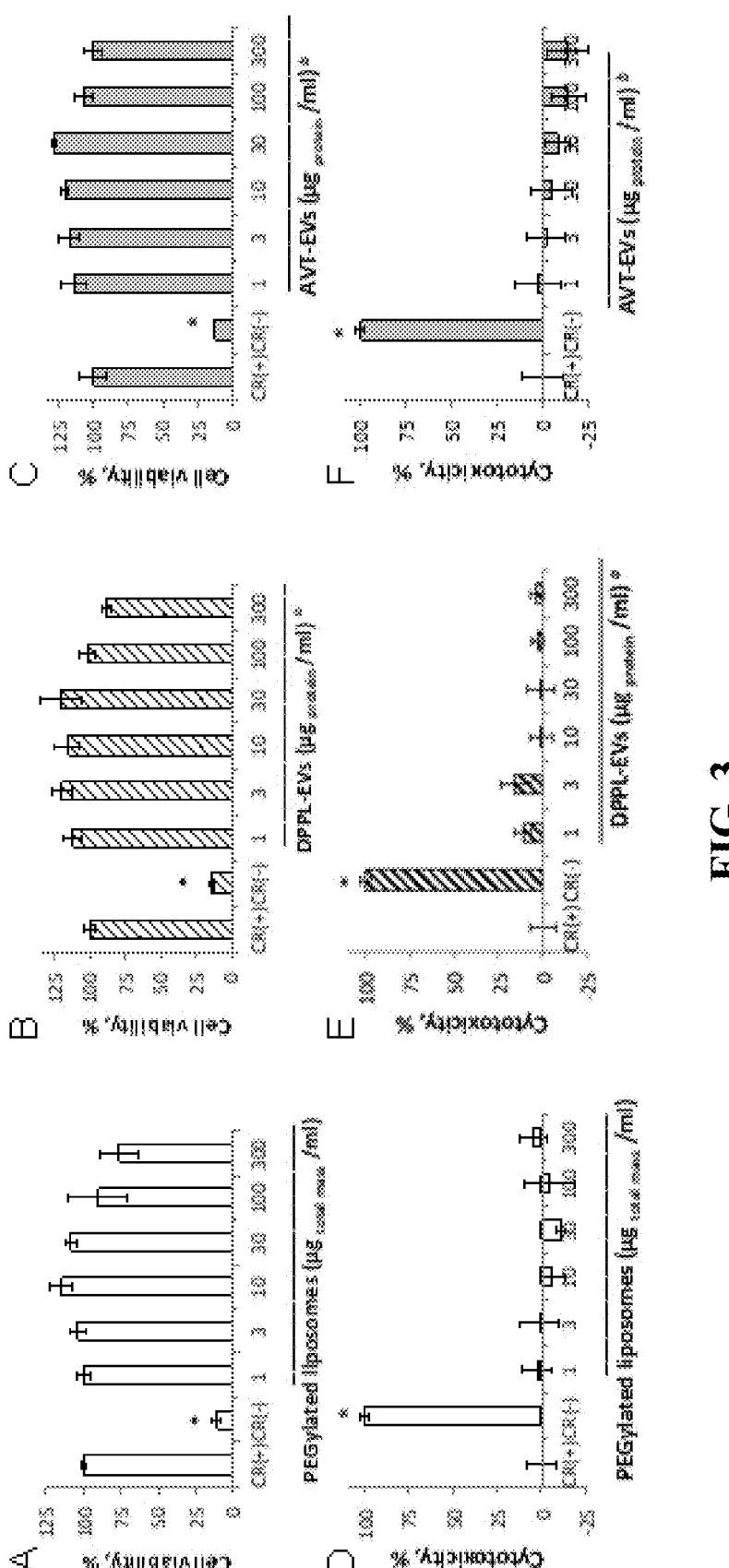
FIG. 3. Biocompatibility of placental DPPL-EVs and apical AVT EVs in NCI-H441 cells after 24-hour exposure. Blank media (no treatment) was used as positive control set as 100% viability (A-C) and 0% cytotoxicity (D-F), Triton X-100 was used as negative control. PEGylated unloaded liposomes were also used as a control for comparison to the EV populations. CR(+), positive control (no treatment); CR(−), negative control (0.1% v/v Triton X-100). Error bars indicate standard deviation (n=3 per group). * P<0.05 by ANOVA. $^a$DPPL-EVs, percent protein of the total mass=33.9%; $^b$apical AVT-EVs, percent protein of the total mass=18.6%.

Biocompatibility of placentally derived EVs. The human lung adenocarcinoma cell line NCI-H441 (FIG. 3) and primary human pulmonary microvascular endothelial cells (HPMEC) (data not shown) were utilized to determine the effect of blank (not loaded with drug) placentally derived EVs on cell viability by the WST-1 assay (A-C) and cytotoxicity by the LDH assay (D-F). These experiments were carried out to ensure that the proposed drug carrier materials themselves (placentally derived EVs) will not cause cellular damage. In the WST-1 assay, a significant reduction in cell viability (as seen for the negative control, Triton X-100) would indicate concerns for the biocompatibility of the biomaterial. FIG. 3 (A-C) shows that for both DPPL-EVs and apical AVT-EVs, in the range of concentrations tested (1-300 μg total mass/mL), no significant reduction in cell viability was observed compared to the positive control (cell culture medium, set at 100% cell viability).

In the LDH assay, the cytotoxicity of various treatments is compared to that of the negative control (Triton X-100, set to 100% cytotoxicity) and the positive control (cell culture medium, set to 0% cytotoxicity). FIG. 3 (D-F) shows that in the range of concentrations tested, neither DPPL-EVs nor apical AVT-EVs elicited a significant cytotoxic response. This indicates that the nanovesicles themselves as drug carriers are not expected to cause any adverse effects upon the cells. This is not to be confused with the use of the WST-1 assay below (in FIG. 4), which shows the cytotoxic pharmacologic effect of paclitaxel in reducing the cell viability of the same NCI-H441 cell line as a result of the drug treatment.

Drug loading of paclitaxel into placentally derived EVs. One mL of empty apical AVT-EVs stored in sterile PBS was added to 1 mL of paclitaxel solution prepared in ethanol (5 mg/mL). Ethanol was only used to solubilize the paclitaxel in order to introduce paclitaxel into the formulation, as reported previously by Kim et al.[8] The ethanol was subsequently removed and is not present in the formulation administered to cells in vitro nor to animals in vivo. This mixture was subjected to 6 cycles of sonication. Each cycle included 30 seconds of sonication at 20% amplitude and 30 seconds off followed by a 2-minute cooling period on ice. At the end of the 6th cycle of sonication, the formulation was stored at room temperature for 1 hour. After 1 hour, the formulation was stored at 4° C. The Z-average particle size was measured using dynamic light scattering and drug loading was determined by removing free (unentrapped) drug from the paclitaxel-loaded nanovesicles by ultracentrifugation. 4.5 mL of PBS was added to 500 μL of the nanoformulation, which was then centrifuged at 48,000 rpm for 2 hours at 4° C. The collected supernatant was measured for paclitaxel concentration using our previously published HPLC method[31] and the encapsulation efficiency was calculated as previously described,[32] utilizing lyophilization to quantify total vesicle mass. The resulting paclitaxel-loaded apical AVT-EVs were 400.7±51.3 nm in diameter with 40.8% drug loading, and the encapsulation efficiency was determined to be 97.9%. For comparison, the drug loading of Abraxane is approximately 10%.[34-36]

Figure 4:
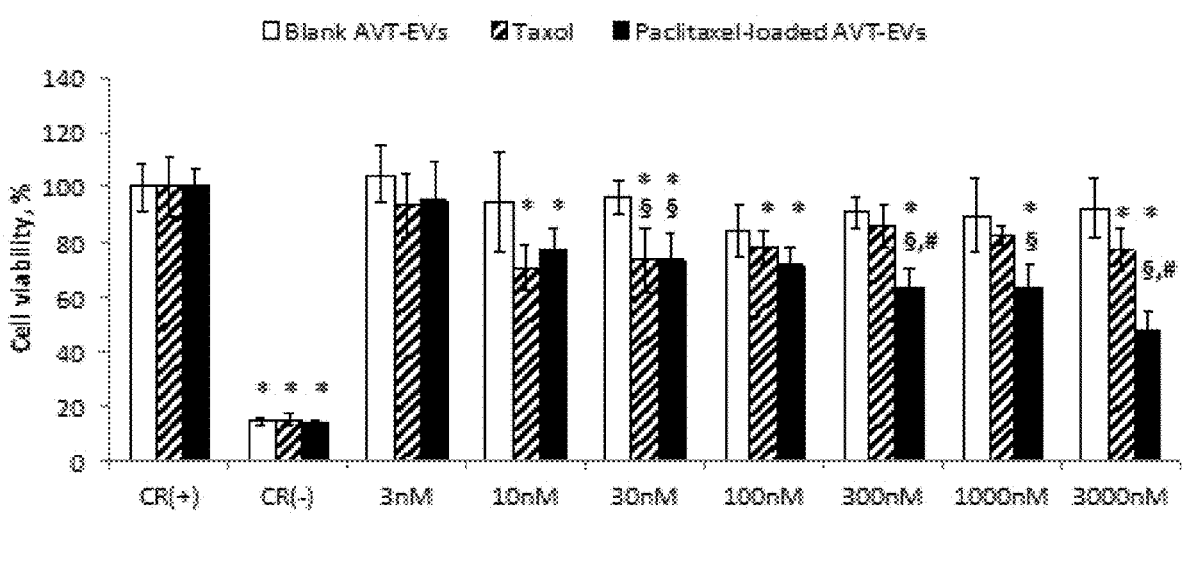
FIG. 4. NCI-H441 cell viability after 24-hour exposure to blank apical AVT-EVs, Taxol and paclitaxel-loaded apical AVT-EVs as assessed by the WST-1 colorimetric assay. CR(+), positive control (no treatment); CR(−), negative control (0.1% v/v Triton X-100). Error bars indicate standard deviation (n=3-6 per group). Asterisk (*) indicates significant difference between each treatment and its corresponding positive control (P<0.05). § P<0.05 for Taxol and paclitaxel-loaded apical AVT-EVs treatments vs. the corresponding blank apical AVT-EVs in each group. #P<0.05 for treatment with paclitaxel-loaded apical AVT-EVs vs. the corresponding Taxol treatment in each group.

Effect of paclitaxel-loaded apical AVT-EVs to reduce the cell viability of lung cancer cells in vitro. FIG. 4 shows that paclitaxel-loaded apical AVT-EVs reduced NCI-H441 cell viability to a significantly greater extent than did Taxol at both 300 nM and 3000 nM, as measured by the WST-1 assay. Both formulations reduced cell viability at most concentrations, and in confirmation of the results shown previously in FIG. 3, none of the blank nanovesicles (not containing drug) at equivalent nanocarrier concentrations caused any significant reduction in cell viability.

Figure 5:
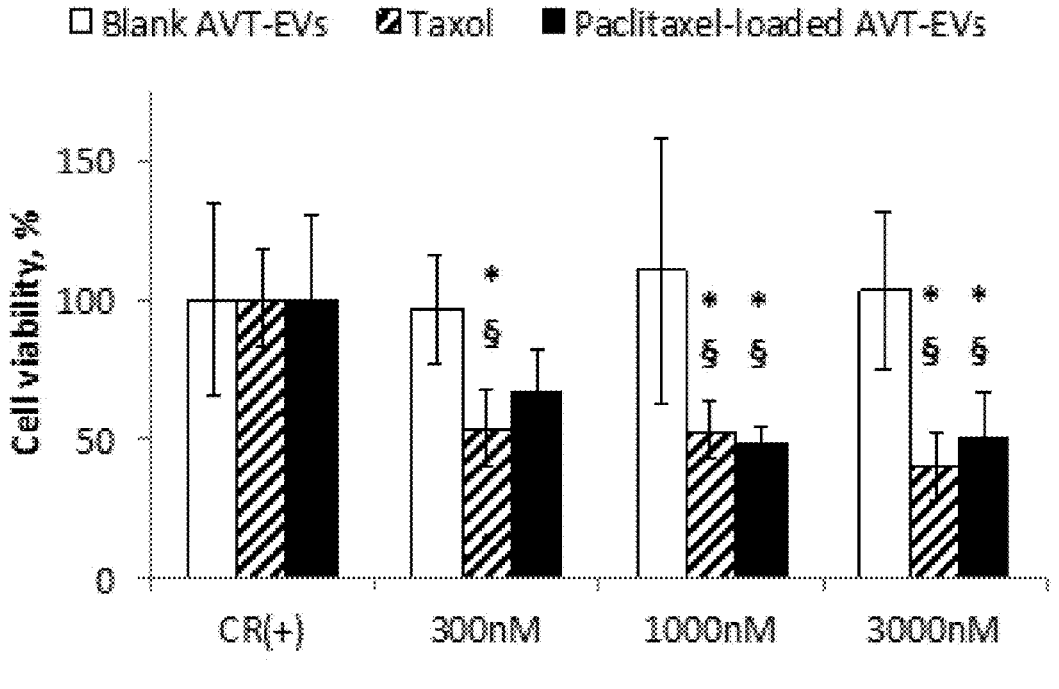
FIG. 5. NCI-H441 cell viability after 24-hour exposure to blank apical AVT-EVs, Taxol, and paclitaxel-loaded apical AVT-EVs as assessed with the Trypan blue exclusion test. CR(+), positive control (no treatment). Error bars indicate standard deviation (n=4-8 per group). Asterisk (*) indicates significant difference between each treatment and its corresponding positive control (P<0.05). § P<0.05 for Taxol and paclitaxel-loaded apical AVT-EVs treatments vs corresponding blank apical AVT-EVs in each group.

Likewise, the Trypan blue exclusion assay (FIG. 5) also demonstrated significant reductions in NCI-H441 cell viability after 24-hour exposure to both Taxol and paclitaxel-loaded apical AVT-EVs. These data show that the encapsulation of paclitaxel into apical AVT-EVs does not hinder its pharmacological effect upon cancer cells.

In vivo tissue distribution of paclitaxel in CD-1 mice following tail-vein injection of Abraxane or paclitaxel-loaded apical AVT-EVs. Tissue distribution of paclitaxel following IV injection (via tail vein) of either Abraxane or paclitaxel-loaded apical AVT-EVs were compared in Hsd:

ICR (CD-1) mice (Envigo, Indianapolis, IN). All mice used in this experiment were handled in accordance with an approved protocol from UTMB's Institutional Animal Care and Use Committee. Abraxane was obtained from Abraxis BioScience (Los Angeles, CA) and paclitaxel-loaded apical AVT-EVs (PTX-apical AVT-EVs) were prepared as described above. Each animal received a dose of 5 mg/kg. At predetermined time points (5 min, 15 min, 30 min, 1 h, 2 h, 4 h, 6 h, and 8 h), each animal was sacrificed by $CO_2$ asphyxiation and the following tissues were resected for quantification of paclitaxel concentration: lung, liver, spleen, and kidney. The experiments were performed in duplicate. For control, animals were injected with blank apical AVT-EVs (without paclitaxel), and these control animals were sacrificed after 5 minutes and the same organs were used to establish the baseline levels and calibration curves for the analytical method.

Samples were analyzed with an API 4000 triple quadrupole mass spectrometer coupled with an Agilent HPLC 1200 system (Applied Biosystems, Foster City, CA). Separation of paclitaxel was achieved with a Waters Symmetry C18 HPLC column at 25° C. The mobile phase contained (A) methanol with 0.1% formic acid and (B) 0.1% formic acid aqueous solution (v/v) with a gradient elution of 0-5 min, 70% A, 5.1-7.1 min, 90% A, and 7.1-13.0 min, 70% A, at a flow rate of 300 μL/min. d5-Paclitaxel was used as the internal standard. Multiple Reaction Monitoring was set up at m/z 876-308 for paclitaxel (PTX) and m/z 881-313 for d5-paclitaxel. Tissue concentrations were quantified by accurately weighing 40 mg of tissue into a Biomasher II 1.5 mL tube, to which 100 μL of saline were added. The tissue was mashed with the plastic piston until no observable pieces remained. The internal standard working solution (10 μL) and acetonitrile (700 μL) were then added. The mixture was shaken for 3 min, followed by centrifugation at 12,000×g for 15 min. The solution was then transferred into a new tube and dried under a stream of nitrogen at 40° C. The residue was then reconstituted with 300 μL of initial mobile phase and 10 μL were injected into the HPLC system. Partial validation of the method was performed for an initial calibration range of 0.312 to 50.0 μg/g in liver, lung, spleen, and kidney. Calibration standards were prepared by spiking known concentrations of paclitaxel into tissue homogenate from animals in the control group receiving an injection of vehicle only.

Table 3 compares the tissue concentrations of paclitaxel in the lungs, liver, spleen, and kidneys after 5 mg/kg IV injections of either Abraxane or PTX-apical AVT-EVs in CD-1 mice over eight hours (n=2 per formulation).

TABLE 3

Tissue concentrations of paclitaxel (μg/g) in CD-1 mice at various time points after a 5 mg/kg IV injection of Abraxane ® or paclitaxel-loaded apical AVT-EVs (PTX-apical AVT-EVs). Data are presented as mean ± S.D. (n = 2 per time point).

| Time (h) | Abraxane | | | | PTX-apical AVT-EVs | | | |
| | lungs | liver | spleen | kidneys | lungs | liver | Spleen | kidneys |
|---|---|---|---|---|---|---|---|---|
| 0.08 | 7.8 ± 0.3 | 37.5 ± 8.1 | 5.5 ± 1.2 | 12.9 ± 0.4 | 219.3 ± 63.3 | 29.6 ± 7.9 | 11.5 ± 0.4 | 4.4 ± 1.8 |
| 0.25 | 5.1 ± 0.7 | 33.7 ± 3.0 | 4.9 ± 0.6 | 8.0 ± 0.3 | 215.8 ± 50.6 | 23.0 ± 1.8 | 11.3 ± 2.7 | 3.7 ± 0.9 |
| 0.5 | 3.4 ± 0.9 | 26.8 ± 3.3 | 4.2 ± 0.4 | 6.3 ± 0.4 | 193.0 ± 91.9 | 32.1 ± 2.3 | 17.7 ± 3.7 | 4.8 ± 1.8 |
| 1 | 3.0 ± 0.7 | 20.5 ± 3.7 | 4.3 ± 0.8 | 5.5 ± 0.2 | 202.0 ± 2.1 | 29.7 ± 0.8 | 17.9 ± 5.2 | 3.3 ± 0.4 |
| 2 | 2.2 ± 0.5 | 17.8 ± 4.9 | 3.2 ± 0.5 | 5.2 ± 0.2 | 93.5 ± 48.8 | 34.3 ± 7.4 | 24.8 ± 10.5 | 2.5 ± 0.7 |
| 4 | 0.8 ± 0.1 | 4.1 ± 0.8 | 1.4 ± 0.6 | 1.3 ± 0.5 | 127.6 ± 67.7 | 36.9 ± 2.5 | 51.8 ± 2.1 | 2.2 ± 0.1 |
| 6 | 0.5 ± 0.1 | 2.4 ± 0.1 | 0.7 ± 0.1 | 0.7 ± 0.0 | 107.3 ± 26.5 | 44.6 ± 9.3 | 51.6 ± 27.0 | 1.7 ± 0.1 |
| 8 | 0.4 ± 0.0 | 2.7 ± 0.3 | 0.5 ± 0.2 | 0.4 ± 0.0 | 104.5 ± 48.1 | 39.5 ± 6.3 | 40.2 ± 0.6 | 1.6 ± 0.2 |

Figure 6:
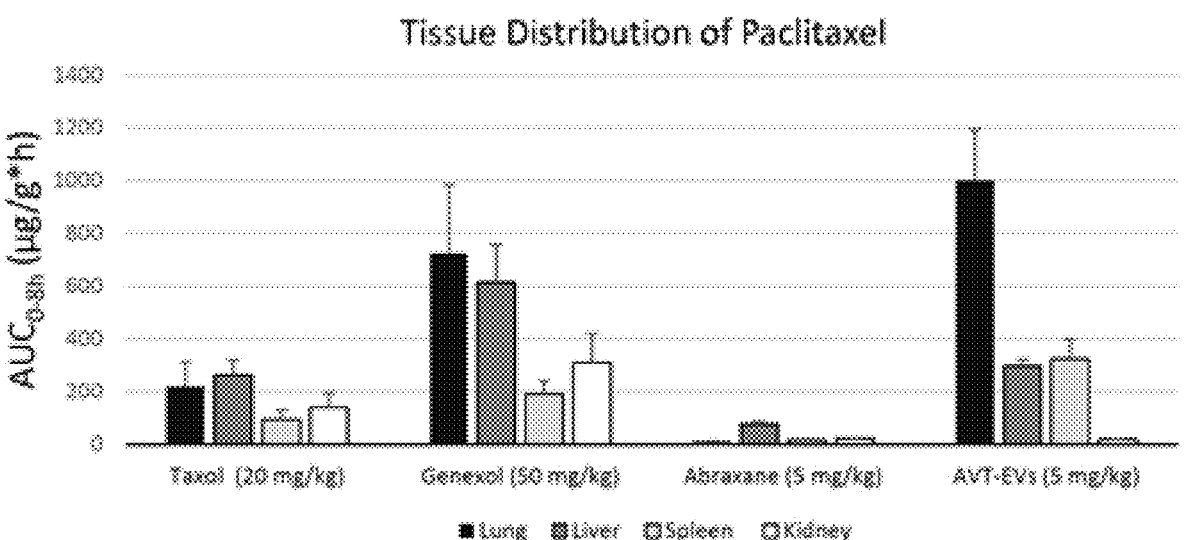
FIG. 6. Tissue distribution of paclitaxel as calculated by the area under the tissue concentration vs. time curve for the first 8 hours following IV injection of Taxol (20 mg/kg, n=4), Genexol-PM (50 mg/kg, n=4), Abraxane (5 mg/kg, n=2), or paclitaxel-loaded apical AVT-EVs (5 mg/kg, n=2). The data for Taxol and Genexol come from the literature [Kim et al., 2001] for B16 melanoma-induced SPF C57BL/6 mice, and the data for Abraxane and PTX-apical AVT-EVs were determined in our lab using CD-1 mice. All tissue $AUC_{0-8h}$ data are reported as μg·h/g.
Figure 7:
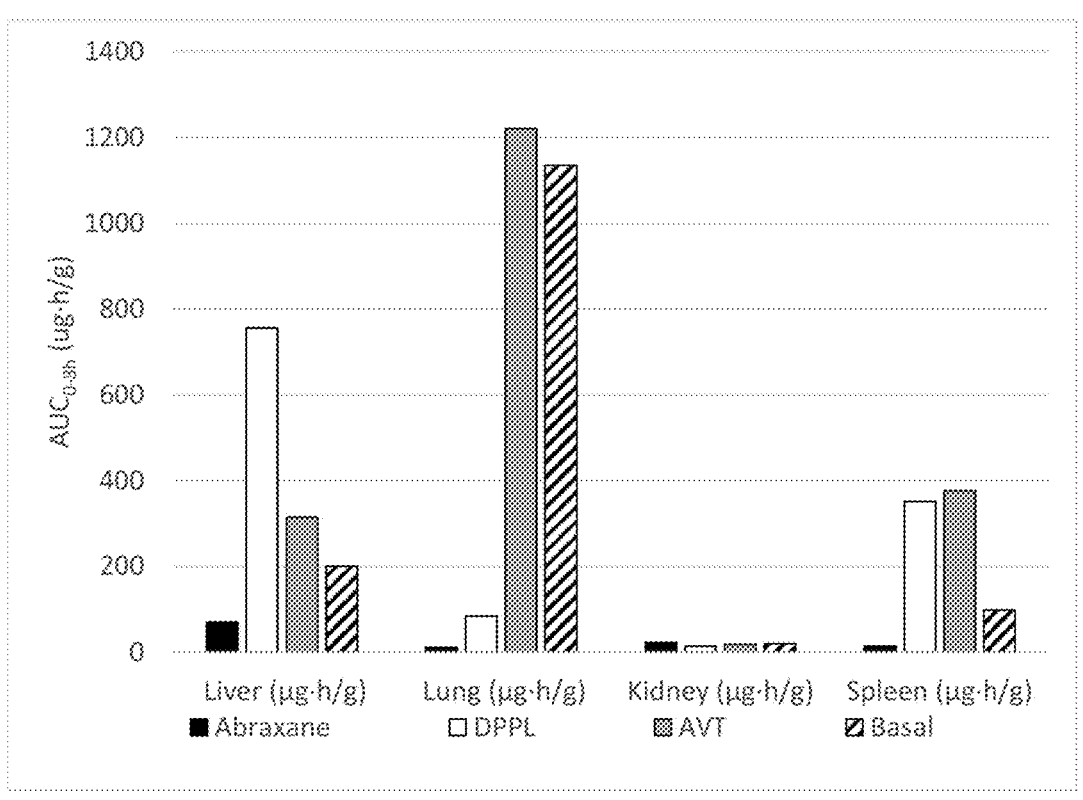
FIG. 7. Cumulative tissue distribution ($AUC_{0-8h}$) of paclitaxel 8 h after i.v. administration of Abraxane (marketed nanoformulation) or three different nanovesicle preparations in CD-1 mice. All doses were 5 mg/kg.

An area under the tissue concentration vs. time curve ($AUC_{0-8h}$) value was calculated by the trapezoidal rule, as described previously by Kim et al.[33] FIG. 6 shows the results of the comparison of Abraxane tissue distribution to PTX-apical AVT-EVs following IV injection of 5 mg/kg of each formulation (n=2). Within the same figure, these data were compared to tissue distribution results reported by Kim et al. for tissue concentration $AUC_{0-8h}$ following intravenous injection of Taxol® (PTX in Cremophor EL) or Genexol®-PM (a polymeric micelle formulation of PTX approved in Korea for the treatment of lung cancer) in murine B16 melanoma-induced SPF C57BL/6 mice (n=4).

FIG. 6 shows a significant distribution of paclitaxel to the lungs of mice that received an IV injection of 5 mg/kg of PTX-loaded apical AVT-EVs as compared to the lung distribution of other paclitaxel formulations as well as compared to the distribution of paclitaxel in other organs. The area under the tissue concentration-time curve ($AUC_{0-8h}$) of PTX in the lungs of mice given PTX-apical AVT-EVs was 85-fold higher than the $AUC_{0-8h}$ of PTX in the lungs of mice treated with 5 mg/kg of Abraxane. In addition, the lung $AUC_{0-8h}$ for the PTX-apical AVT-EVs was 1.4-fold higher than the $AUC_{0-8h}$ in the lungs of mice treated with 50 mg/kg of Genexol-PM (a dose that is 10× higher than the dose of the PTX-apical AVT-EVs). Furthermore, the highest tissue accumulation of paclitaxel following the injection of Abraxane was in the liver (6.5-fold higher than in the lung, in which the drug tissue $AUC_{0-8h}$ was the lowest of the four organs). On the other hand, following injection of the PTX-apical AVT-EVs, the $AUC_{0-8h}$ of PTX in the lungs was more than 3× higher than the $AUC_{0-8h}$ in either the liver or the spleen, and more than 50× greater than in the kidneys. These results highlight the potential of the AVT-EVs to deliver substantially more paclitaxel to the lungs than two nanoformulations that have been approved for treating lung cancer. The comparatively reduced accumulation of paclitaxel into other organs is promising for potentially reduced side effects in off-target tissues.

The data presented show that: (i) apical AVT-EVs and DPPL-EVs express markers confirming syncytiotrophoblast origin with minimal contamination and their physicochemical properties are similar to those of nanocarriers used as drug delivery systems. (ii) DPPL-EVs have strong expression of so-called "exosome-enriched markers" CD81, CD9, CD63, TSG101, and ALIX, and lower surface expression of efflux transporters P-glycoprotein and BCRP. (iii) Both populations of EVs are stable for at least 28 days at 4° C. and 22° C. and for 24 hours at 37° C. (iv) Both sets of EVs are biocompatible with lung epithelial (NCI-H441) and endothelial (HPMEC) cells. (v) Paclitaxel can be loaded into apical AVT-EVs (40.8% by mass) with 97.9% encapsulation efficiency. (vi) apical AVT-EVs loaded with paclitaxel (PTX) reduced NCI-H441 cell viability by 50%. (vii) After IV injection of 5 mg/kg of PTX-loaded apical AVT-EVs, the area under the tissue concentration-time curve ($AUC_{0-8h}$) of PTX in the lungs of mice was 85-fold higher than the $AUC_{0-8h}$ of PTX in the lungs of mice treated with 5 mg/kg of Abraxane and 1.4-fold higher than the $AUC_{0-8h}$ in the lungs of mice treated with 50 mg/kg of Genexol-PM®. (viii) Following IV administration of 5 mg/kg of PTX-loaded apical AVT-EVs, the $AUC_{0-8h}$ of PTX in the lungs of mice (999.5±193.0 μg·h/g of tissue) was substantially higher than the $AUC_{0-8h}$ in the spleen (324.9±74.7 μg·h/g), liver (296.9±25.2 μg·h/g) and kidney (19.0±1.7 μg·h/g), indicating preferential migration to the lung tissue.

Example 2

Administration of the Drug-Loaded Nanovesicles Via Inhalation

Drug-loaded apical AVT-EVs can be delivered to the lung via inhalation (nebulization of an aqueous apical AVT-EV suspension).

Table 4 below shows the concentration of paclitaxel in the lung, liver, and plasma after administering the paclitaxel-loaded apical AVT-EVs via nebulization at various doses. While appreciable levels of the drug were measured in the lung tissue, the drug could not be detected in the liver nor in the plasma, indicating reduced off-target effects. It should be noted that the tissue concentration of paclitaxel in the lung following the nebulization of the lowest dose investigated (1 mg/kg) is similar to the concentration found 5 minutes after i.v. administration of 5 mg/kg Abraxane (7.8±0.3 μg/g; please see Table 3). However, the i.v. administration of Abraxane resulted in tissue concentrations in the liver that exceeded concentrations in the lung by 4.8-fold, whereas following nebulization of the drug-loaded apical AVT-EVs, no detectable amount of paclitaxel could be found in the liver.

TABLE 4

Paclitaxel concentration in the lung, liver, and plasma after nebulization of an aqueous suspension of paclitaxel-loaded apical AVT-EVs.

| Mice and dosage | Lung Conc. (μg/g) | Liver Conc. (μg/g) | Plasma Conc. (μg/mL) |
|---|---|---|---|
| Mouse #1, 1 mg/kg | 7.00 | <LLOQ | <LLOQ |
| Mouse #2, 1 mg/kg | 8.38 | <LLOQ | <LLOQ |
| Mouse #3, 1 mg/kg | 9.17 | <LLOQ | <LLOQ |
| Mouse #4, 1.5 mg/kg | 19.0 | <LLOQ | <LLOQ |
| Mouse #5, 1.5 mg/kg | 18.7 | <LLOQ | <LLOQ |
| Mouse #6, 1.5 mg/kg | 4.33 | <LLOQ | <LLOQ |
| Mouse #7, 2 mg/kg | 14.6 | <LLOQ | <LLOQ |
| Mouse #8, 2 mg/kg | 25.1 | <LLOQ | <LLOQ |

* The calibration range is 0.625-100 μg/mL for plasma samples and 0.312-50.0 μg/g for organ samples.
Nebulization doses are calculated based on the breathing zone estimates reported by Phillips et al.[59]

Example 3

Administration of Anti-Viral Loaded Apical AVT-EVs

As an example of utilizing this technology to load a therapeutic compound from another drug class, efavirenz was used as a model drug among those that may be used to treat lower respiratory tract infections and their complications. Efavirenz was loaded (10% by mass) into apical AVT-EVs using the aforementioned sonication method, except that the drug was first prepared in ethanol at a concentration of 10 mg/mL. The Z-average particle size, polydispersity index (PDI), and encapsulation efficiency were determined after overnight storage at 4° C. The average characteristics from two batches of the efavirenz-loaded apical AVT-EVs prepared on separate days were as follows: Z-average particle size: 551 nm, PDI: 0.31, and encapsulation efficiency: 95.8%.

The efavirenz-loaded apical AVT-EVs were subsequently injected via tail vein into CD-1 mice at a dose of 5 mg/kg and compared to a control injection of 5 mg/kg of conventional efavirenz (dissolved with DMSO). Plasma and tissue concentrations were determined by LC-MS/MS. The table below shows the enhanced distribution of this drug to the lungs when administered as the apical AVT-EV formulation as compared to conventional administration.

TABLE 5

Plasma and tissue concentrations (liver and lung) of efavirenz at various time points after tail vein administration of conventional efavirenz (in DMSO) versus efavirenz-loaded apical AVT-EVs. Both formulations were administered at a dose of 5 mg/kg in mice. <LLOQ indicates that the concentration in the tissue was below the lower limit of quantitation (35 ng/g).

| Time (h) | Efavirenz in DMSO dose 5 mg/kg | | | Efavirenz- apical AVT-EVs dose 5 mg/kg | | |
|---|---|---|---|---|---|---|
| | Plasma (ng/mL) | Liver (ng/g) | Lungs (ng/g) | Plasma (ng/mL) | Liver (ng/g) | Lungs (ng/g) |
| 0.083 | 4096 | 7586 | 2140 | 2574 | 1557 | 6202 |
| 0.25 | 2825 | 5422 | 802 | 1794 | 1921 | 6980 |
| 0.5 | 1616 | 5228 | 830 | 1053 | 1615 | 3446 |
| 1 | 1562 | 176 | 273 | 748 | 1159 | 1571 |
| 2 | 724 | 135 | [missing] | 274 | 1366 | 514 |
| 3 | 396 | 136 | <LLOQ | 248 | 175 | 161 |
| 4 | 103 | 137 | <LLOQ | [missing] | 137 | 138 |
| 6 | 64.4 | 115 | <LLOQ | 100 | <LLOQ | <LLOQ |
| 8 | 33.1 | <LLOQ | <LLOQ | 166 | <LLOQ | <LLOQ |

The area under the plasma-time concentration curve from 0-8 hours ($AUC_{0-8h}$) was calculated for both formulations and determined to be 4.52 µg·h/mL for conventional administration, but only 2.97 µg·h/mL in the plasma after administration of the apical AVT-EV formulation, which indicates that when using the lung-targeting apical AVT-EV formulation, less drug is in the plasma because more is directed to lung tissue. This is further verified by the increased area under the tissue concentration-time curve ($AUC_{0-8h}$) for efavirenz in the lungs from the apical AVT-EV formulation (5.58 µg·h/g), which was 5.9-fold higher than the $AUC_{0-8h}$ following conventional administration (0.95 µg·h/g). Furthermore, less efavirenz accumulated in the liver when administered as the apical AVT-EV formulation as compared to conventional dosing. With conventional administration, the lung:liver tissue $AUC_{0-8h}$ ratio was 0.19, meaning that the overall exposure of the liver to the drug was approximately 5-times higher than the cumulative amount of drug distributed to the lungs. When administered as the apical AVT-EV formulation, on the other hand, 46% more drug was cumulatively detected in the lungs than in the liver.

Example 4

In Vivo Toxicity Testing of Apical AVT-EVs

Male mice were randomly divided into six groups (n=5 per group), weighed (day 0), and received a single intravenous tail injection of plain apical AVT-EVs (1 µg$_{protein}$/g, 3 µg$_{protein}$/g, 6 µg$_{protein}$/g, 12 µg$_{protein}$/g, and 24 µg$_{protein}$/g of body weight); the control group of animals received an intravenous tail injection of PBS only. Animals were monitored for visible signs of toxicity and behavioral changes 4 times on the day of injection, followed by 2 times daily during the next 4 days, and then once daily until the end of the study on the 14$^{th}$ day using Clinical Scores (1-5). Score 1 was assigned to healthy animals; Score 2 was for animals with ruffled fur or showing signs of lethargy; Score 3 was for animals with score 2 plus 1 additional clinical sign such as hunched posture or orbital tightening; Score 4 was for animals with score 3 plus 1 additional clinical sign such as reluctance to move when stimulated; Score 5 for animals with an inability to react to food/water normally, or any neurologic signs (seizures, tremors, head tilt, paralysis) or found moribund. The animals were also weighed at the end of the study (on day 14), and weight changes were assessed in absolute units (g).

TABLE 6

Effect of blank apical AVT-EVs on the weight of CD1 male mice.

| Dose of AVT-EVs (µg/g) | Weight of mice (g) on Day 0 Mean ± SD | Weight of mice (g) on Day 14 Mean ± SD |
|---|---|---|
| 0 | 29.1 ± 1.3 | 31.8 ± 1.6 |
| 1 | 28.7 ± 1.6 | 31.5 ± 1.1 |
| 3 | 28.9 ± 1.5 | 32.4 ± 1.6 |
| 6 | 29.1 ± 2.3 | 33.1 ± 2.3 |
| 12 | 28.4 ± 2.2 | 32.0 ± 3.2 |
| 24 | 28.9 ± 2.1 | 34.4 ± 2.7 |

In the in vivo toxicity study, we did not observe any visible signs of toxicity or behavior changes in CD1 male mice during 14 days following a single i.v. injection of apical AVT-EVs in the concentration range of 1-24 µg protein/g. All animals survived, and Table shows that there were no significant differences in the initial and final weights among the tested groups. Taken together, these data and the lack of observed cytotoxicity even at the highest concentrations tested in vitro suggest that placental apical AVT-EVs could potentially be used as a drug delivery vehicle.

Example 5

Preparation and Characterization of Vesicles from Basal Placental Membranes

Vesicles from basal membranes were prepared and characterized. The Z-average diameter of the basal vesicles was 404±37 nm, with a polydispersity index of 0.51±0.03. Paclitaxel was loaded into the basal vesicles with >97% encapsulation efficiency. Figure shows that after i.v. injection of 5 mg/kg of paclitaxel-loaded AVT-EVs, the area under the tissue concentration-time curve ($AUC_{0-8h}$) of paclitaxel in the lungs of mice was 95-fold higher than the $AUC_{0-8h}$ of PTX in the lungs of mice treated with 5 mg/kg of Abraxane® (an albumin nanoparticle formulation of paclitaxel currently on the market). Similarly, the lung $AUC_{0-8h}$ of paclitaxel was 88-fold higher than that of Abraxane after administration of Basal-EVs.

Example 6

Expression of Major Histocompatibility Complex (MHC) Proteins in Placental EVs

As a first step in the characterization of the immunogenicity of placental EVs, we determined the expression of several allotypes of human leukocyte class I and class II histocompatibility antigens (HLA) (Table 7). The proteomic analysis revealed total spectrum counts for several HLA-I allotypes including HLA-A, HLA-B, HLA-Cw, HLA-E, HLA-F, and HLA-G. The relative average expression of allotypes HLA-A, HLA-B, and HLA-C in AVT-EVs was higher than the expression of HLA-G, HLA-E, and HLA-F. On the other hand, the relative average expression of class II allotypes, namely HLA-DM, HLA-DR and HLA DRB was several fold lower than the expression of HLA-I allotypes. The relatively low to no expression of HLA-I and HLA-II molecules in the apical AVT-EVs suggest that these EVs have favorable properties with respect to immunogenicity.

TABLE 7

Expression of major histocompatibility complex (MHC) proteins in apical AVT-EVs,
Basal-EVs, or DPPL-EVs.

| Protein Name | Accession Number | Molecular Weight | DPPL-EVs | AVT-EVs | Basal-EVs |
|---|---|---|---|---|---|
| HLA class I histocompatibility antigen, B-38 alpha chain OS = *Homo sapiens* OX = 9606 GN = HLA-B PE = 1 SV = 1 | Q95365 | 40 kDa | 9.35 | 3.58 | 22.42 |
| HLA class I histocompatibility antigen, B-40 alpha chain OS = *Homo sapiens* OX = 9606 GN = HLA-B PE = 1 SV = 1 | Q04826 | 41 kDa | 10.52 | 3.58 | 20.47 |
| HLA class I histocompatibility antigen, B-35 alpha chain OS = *Homo sapiens* OX = 9606 GN = HLA-B PE = 1 SV = 1 | P30685 | 40 kDa | 9.35 | 4.47 | 18.52 |
| HLA class I histocompatibility antigen, A-11 alpha chain OS = *Homo sapiens* OX = 9606 GN = HLA-A PE = 1 SV = 1 | P13746 | 41 kDa | 10.52 | 2.68 | 18.52 |
| HLA class I histocompatibility antigen, A-2 alpha chain OS = *Homo sapiens* OX = 9606 GN = HLA-A PE = 1 SV = 1 | P01892 | 41 kDa | 8.18 | 3.58 | 17.54 |
| HLA class I histocompatibility antigen, A-24 alpha chain OS = *Homo sapiens* OX = 9606 GN = HLA-A PE = 1 SV = 2 | P05534 | 41 kDa | 8.18 | 2.68 | 17.54 |
| HLA class I histocompatibility antigen, A-34 alpha chain OS = *Homo sapiens* OX = 9606 GN = HLA-A PE = 1 SV = 1 | P30453 | 41 kDa | 8.18 | 2.68 | 16.57 |
| HLA class I histocompatibility antigen, Cw-6 alpha chain OS = *Homo sapiens* OX = 9606 GN = HLA-C PE = 1 SV = 2 | Q29963 | 41 kDa | 7.01 | 1.79 | 17.54 |
| HLA class I histocompatibility antigen, alpha chain G OS = *Homo sapiens* OX = 9606 GN = HLA-G PE = 1 SV = 1 | P17693 | 38 kDa | 8.18 | 1.79 | 6.82 |
| HLA class I histocompatibility antigen, alpha chain E OS = *Homo sapiens* OX = 9606 GN = HLA-E PE = 1 SV = 4 | P13747 | 40 kDa | 2.34 | 0.89 | 9.75 |
| HLA class II histocompatibility antigen, DR alpha OS = *Homo sapiens* OX = 9606 GN = HLA-DRA PE = 1 SV = 1 | P01903 | 29 kDa | 2.34 | 0.00 | 7.80 |
| HLA class I histocompatibility antigen, alpha chain F OS = *Homo sapiens* OX = 9606 GN = HLA-F PE = 1 SV = 3 | P30511 | 39 kDa | 2.34 | 0.89 | 5.85 |
| HLA class II histocompatibility antigen, DRB1-15 beta chain OS = *Homo sapiens* OX = 9606 GN = HLA-DRB1 PE = 1 SV = 2 | P01911 | 30 kDa | 1.17 | 0.00 | 3.90 |
| HLA class II histocompatibility antigen gamma chain OS = *Homo sapiens* OX = 9606 GN = CD74 PE = 1 SV = 3 | P04233 | 34 kDa | 0.00 | 0.00 | 1.95 |
| HLA class II histocompatibility antigen, DM beta chain OS = *Homo sapiens* OX = 9606 GN = HLA-DMB PE = 1 SV = 1 | P28068 | 29 kDa | 0.00 | 0.00 | 1.95 |

These results support the development of EVs derived from human syncytiotrophoblast as delivery vehicles to treat diseases of the lung.

REFERENCES

1. Lapaire et al., Placenta. 2007; 28(1):1-5.
2. Nabers et al., Thorax. 1990; 45(5):416-418. PMC462498
3. Tong et al., Reproduction (Cambridge, England). 2017; 153(6):835-845.
4. Torre et al., Advances in experimental medicine and biology. 2016; 893:1-19.
5. Howlader et al., (eds SEER Cancer Statistics Review (CSR) 1975-2014. National Cancer Institute. 2016; Available at: URL seer.cancer.gov/archive/csr/1975_2014/. Feb. 4, 2019. Updated: Apr. 1, 2017
6. Ettinger et al., Journal of the National Comprehensive Cancer Network: JNCCN. 2017; 15(4):504-535.
7. Lilenbaum, Overview of the initial treatment of advanced non-small cell lung cancer. UpToDate Wolters Kluwer Health. Available at: URL www.uptodate.com/contents/overview-of-the-initial-treatment-of-advanced-non-small-cell-lung-cancer?topicRef=4639&source=see_link. Accessed: Feb. 4, 2019. Updated: Oct. 11, 2018
8. Kim et al., Nanomedicine: nanotechnology, biology, and medicine. 2016; 12(3):655-664. PMC4809755
9. Saari et al., Journal of controlled release. 2015; 220(Pt B):727-737.
10. Hood and Wickline, Wiley interdisciplinary reviews Nanomedicine and nanobiotechnology. 2012; 4(4):458-467.
11. Kalra et al., Proteomics. 2013; 13(22):3354-3364.
12. Wiklander et al., Journal of extracellular vesicles. 2015; 4:26316. PMC4405624
13. Johnsen et al., Biochimica et biophysica acta. 2014; 1846(1):75-87.
14. Sykes et al., Mediators of inflammation. 2012; 2012: 416739. PMC3368617
15. Figueiredo and Schumacher, Immunology. 2016; 148 (1):13-21. PMC4819144
16. Apps et al., Immunology. 2009; 127(1):26-39. PMC2678179
17. Tong et al., Immunology and cell biology. 2018; 10.1111/imcb.12049.

18. Socinski et al., Journal of clinical oncology 2012; 30(17):2055-2062.

19. Mulcahy et al., Journal of extracellular vesicles. 2014; 3. PMC4122821

20. Agrawal et al., Nanomedicine: nanotechnology, biology, and medicine. 2017; 13(5):1627-36.

21. Yang et al., Pharmaceutical research. 2015; 32(6):2003-2014. PMC4520542

22. Smith et al., Nature. 1974; 252(5481):302-303.

23. Gupta et al., Placenta. 2005; 26(1):59-66.

24. Tannetta et al., PloS one. 2013; 8(2):e56754. PMC3577732

25. Southcombe et al., PloS one. 2011; 6(5):e20245. PMC3102084

26. Nanovskaya et al., The Journal of pharmacology and experimental therapeutics. 2002; 300(1):26-33.

27. Nanovskaya et al., American journal of obstetrics and gynecology. 2013; 209(4):373.

28. Hemauer et al., Biochemical pharmacology. 2009; 78(9): 1272-1278. PMC2748165

29. Afrouzian et al., Biochemical pharmacology. 2018; 156:467-478.

30. Lotvall et al., Journal of extracellular vesicles. 2014; 3:26913. PMC4275645

31. Ali et al., Journal of Liquid Chromatography & Related Tech. 2018; 41(5):232-38.

32. Kalashnikova et al., In: Naik J, ed. Nano Based Drug Delivery. Zagreb, Croatia: IAPC; 2015.

33. Kim et al., Journal of controlled release 2001; 72(1-3): 191-202.

34. Nehate et al., Current drug delivery. 2014; 11(6):666-686.

35. Bhattacharyya et al., Nature communications. 2015; 6:7939. PMC4753781

36. Boschetti-de-Fierro et al., Scientific reports. 2015; 5:18448. PMC4680880

37. Albekairi et al. Therapeutic delivery. 2015; 6(12):1325-1334. PMC497699

38. Rytting et al., Journal of controlled release 2010; 141 (1):101-107.

39. Ali et al., International journal of pharmaceutics. 2013; 454(1):149-157. PMC3800161

40. Ali et al., Therapeutic delivery. 2013; 4(2):161-175. PMC3754434

41. Shah et al., Journal of pharmaceutical research international. 2017; 17(5). PMC5714556

42. DuPage et al., Nature protocols. 2009; 4(7):1064-1072. PMC2757265

43. Kwon and Berns, Molecular oncology. 2013; 7(2):165-177. PMC5528410

44. Choi et al., Drug metabolism and disposition: the biological fate of chemicals. 2013; 41(2):263-269. PMC3558868

45. Spratlin and Sawyer, Critical reviews in oncology/hematology. 2007; 61(3):222-229.

46. Li et al., Cancer biotherapy & radiopharmaceuticals. 2012; 27(4):227-233. PMC3353764

47. Lee et al., Neuro-oncology. 2016; 18(4):486-496. PMC4799693

48. Eiseman et al., Cancer chemotherapy and pharmacology. 1994; 34(6):465-471.

49. Rytting et al., Drug metabolism and disposition: the biological fate of chemicals. 2014; 42(10):1773-1779. PMC4164976

50. Rytting et al., Clinical pharmacokinetics. 2014; 53(6): 545-551. PMC4164383

51. Park et al., Small (Weinheim an der Bergstrasse, Germany). 2018; 14(16):e1703670.

52. Sparreboom et al., Cancer research. 1996; 56(9):2112-2115.

53. Mishra et al., The Annals of thoracic surgery. 2015; 100(4):1167-1174; discussion 1174.

54. Mishra et al., BMC cancer. 2018; 18(1):441. PMC5907356

55. Said et al., The Open Pharmacology Journal. 2007; 1:30-35.

56. UCSF Clinical & Translational Science Institutute. Sample size—Survival analysis. Sample Size Calculators for Designing Clinical Research Available at: URL www.sample-size.net/sample-size-survival-analysis/. Accessed: Nov. 1, 2019. Updated: Jun. 12, 2019

57. Peng et al., International journal of nanomedicine. 2014; 9:3601-3610. PMC4124067

58. Ng et al., Clinical cancer research 2006; 12(14 Pt 1):4331-4338.

59. Phillips et al., J Vis Exp 2017; 122:55454.

The invention claimed is:

1. A full-term placental syncytiotrophoblast derived nanovesicle composition manufactured by (i) mechanically agitating human full-term placental intact villous tissue to generate agitated villous tissue (AVT) nanovesicles having an average diameter of 50 to 800 nm and comprising CD81, CD9, CD63, tumor susceptibility gene 101, programmed cell death 6-interacting protein (ALIX), P-gp, BCRP, and placental alkaline phosphatase (PLAP);

isolating said nanovesicles; and (iii) encapsulating paclitaxel in the isolated AVT nanovesicles at greater than 40 weight percent of total nanovesicles to produce the nanovesicle composition.

2. A method of delivering paclitaxel to a lung of a mammalian subject, the method comprising administering the AVT nanovesicle composition of claim 1, wherein the administering comprises inhalation, parenteral, intravenous, intraarterial, subcutaneous, intratumoral, intramuscular, intraorbital, ophthalmic, intrahepatic, intracapsular, intraperitoneal, intranasal, aerosol, and/or suppository administration.

3. The method of claim 2, wherein the AVT nanovesicles further comprises a synthetic targeting agent comprising an antibody moiety, peptide or small molecule moiety derivatization.

4. The method of claim 2, wherein the AVT nanovesicles more preferentially localize to the subject's lungs compared to administering isolated dual-perfusion of placental lobule (DPPL) extracellular vesicles under the same conditions.

\* \* \* \* \*